US00PP26962P2

(12) United States Plant Patent
Verwer

(10) Patent No.: US PP26,962 P2
(45) Date of Patent: Jul. 19, 2016

(54) ***DAHLIA* PLANT NAMED 'HDSC18'**

(50) Latin Name: *Dahlia hybrida*
Varietal Denomination: HDSC18

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 156 days.

(21) Appl. No.: 14/120,742

(22) Filed: Jun. 21, 2014

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson
(74) *Attorney, Agent, or Firm* — C. A. Whealy

(57) ABSTRACT

A new and distinct cultivar of *Dahlia* plant named 'HDSC18', characterized by its compact, mounding and dense plant habit; dentate to crenate dark-colored leaves; freely flowering habit; daisy-type inflorescence form; large inflorescences with scarlet red-colored ray florets; and good postproduction longevity.

2 Drawing Sheets

Botanical designation: *Dahlia hybrida.*
Cultivar denomination: 'HDSC18'.

BACKGROUND OF THE INVENTION

The present invention relates to a new and distinct cultivar of *Dahlia* plant, botanically known as *Dahlia hybrida*, and hereinafter referred to by the name 'HDSC18'.

The new *Dahlia* plant is a product of a planned breeding program conducted by the Inventor in Lisse, The Netherlands. The objective of the breeding program is to create new compact container *Dahlia* plants with dark-colored leaves, large inflorescences and good postproduction longevity.

The new *Dahlia* plant originated from a cross-pollination conducted by the Inventor in Lisse, The Netherlands in 2008 of *Dahlia hybrida* 'HDPU165', disclosed in U.S. Plant Pat. No. 23,299, as the female, or seed, parent with *Dahlia hybrida* 'VD5-279', not patented, as the male, or pollen, parent. The new *Dahlia* plant was discovered and selected by the Inventor as a single flowering plant from within the progeny of the stated cross-pollination in a controlled greenhouse environment in Lisse, The Netherlands during the summer of 2009.

Asexual reproduction of the new *Dahlia* plant by cuttings since the spring of 2010 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HDSC18'.

These characteristics in combination distinguish 'HDSC18' as a new and distinct *Dahlia* plant:

1. Compact, mounding and dense plant habit.
2. Dentate to crenate dark-colored leaves.
3. Early and freely flowering habit.
4. Daisy-type inflorescence form.
5. Large inflorescences with scarlet red-colored ray florets.
6. Good postproduction longevity.

Plants of the new *Dahlia* differ primarily from plants of the female parent, 'HDPU165', in the following characteristics:

1. Plants of the new *Dahlia* are more freely flowering than plants of 'HDPU165'.
2. Leaves of plants of the new *Dahlia* are not as dark in color as leaves of plants of 'HDPU165'.
3. Plants of the new *Dahlia* and the female parent selection differ in ray floret color as plants of the female parent selection have red purple-colored ray florets.

Plants of the new *Dahlia* differ primarily from plants of the male parent, 'VD5-279', in the following characteristics:

1. Plants of the new *Dahlia* are more compact than plants of 'VD5-279'.
2. Plants of the new *Dahlia* flower for a longer period of time than plants of 'VD5-279'.
3. Plants of the new *Dahlia* are stronger and less susceptible to pathogens than plants of 'VD5-279'.

Plants of the new *Dahlia* can be compared to plants of the *Dahlia hybrida* 'HDCHR23', disclosed in U.S. Plant Pat. No. 26,140. In side-by-side comparisons conducted in Lisse, The Netherlands, plants of the new *Dahlia* differed from plants of 'HDCHR23' in the following characteristics:

1. Plants of the new Dahlia flowered ten days earlier than plants of 'HDCHR23'.
2. Plants of the new *Dahlia* and 'HDCHR23' differed in ray color as plants of 'HDCHR23' have red purple-colored ray florets.
3. Ray florets of plants of the new *Dahlia* were larger than ray florets of plants of 'HDCHR23'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering plants of 'HDSC18'.

The photograph on the second sheet is a close-up view of a typical flowering plant of 'HDSC18'.

DETAILED BOTANICAL DESCRIPTION

The photographs and following observations and measurements describe plants grown during the late summer and early autumn in 15-cm containers in an outdoor nursery in Lisse, The Netherlands and under cultural practices typical of commercial container Dahlia production. During the production of the plants, day temperatures ranged from 15° C. to 30° C. and night temperatures ranged from 10° C. to 20° C. Plants were pinched one time about three weeks after planting. Plants were three months old when the photographs and description were taken. In the following description, color references are made to The Royal Horticultural Society Colour Chart, 1995 Edition, except where general terms of ordinary dictionary significance are used.

Botanical classification: *Dahlia hybrida* 'HDSC18'.

Parentage:

*Female, or seed, parent.*—*Dahlia hybrida* 'HDPU165', disclosed in U.S. Plant Pat. No. 23,299.

*Male, or pollen, parent.*—*Dahlia hybrida* 'VD5-279', not patented.

Propagation:

*Type*.—By vegetative cuttings.

*Time to initiate roots, summer*.—About eleven days at soil temperatures about 15° C.

*Time to initiate roots, winter*.—About 13 days at soil temperatures about 15° C.

*Time to produce a rooted young plant, summer*.—About 22 days at soil temperatures about 15° C.

*Time to produce a rooted young plant, winter*.—About 23 days at soil temperatures about 15° C.

*Root description*.—Fine, fleshy.

*Rooting habit*.—Moderately freely branching; dense.

*Tubers*.—Length: About 15 cm. Diameter: About 15 cm. Texture: Corky. Color: Close to 199B.

Plant description:

*Plant and growth habit*.—Compact and mounding plant habit; inverted triangular plant form; freely basal branching with about eight lateral branches developing per plant; dense and bushy appearance; inflorescences held above the foliar plane on strong peduncles; vigorous growth habit.

*Plant height*.—About 30 cm.

*Plant diameter or spread*.—About 25 cm.

*Lateral branches*.—Length: About 23 cm. Diameter: About 1.8 cm. Internode length: About 5 cm to 15 cm. Texture: Smooth, glabrous. Strength: Strong. Color: Close to 187A.

Leaf description:

*Arrangement*.—Opposite, single or compound with three or five leaflets per leaf

*Leaf length*.—About 7 cm to 18 cm.

*Leaf width*.—About 4 cm to 13 cm.

*Shape*.—Ovate.

*Apex*.—Acute.

*Base*.—Attenuate.

*Margin*.—Dentate to crenate; sinuses divergent.

*Venation pattern*.—Pinnate.

*Texture, upper and lower surfaces*.—Smooth, glabrous.

*Color*.—Developing and fully expanded leaves, upper surface: Close to 200A; venation, close to 187A. Developing and fully expanded leaves, lower surface: Close to 147B; venation, close to 187B, proximally, close to 183B.

*Petioles*.—Length: About 3 cm to 7 cm. Diameter: About 4 mm. Texture, upper and lower surfaces: Smooth, glabrous. Color, upper surface: Close to 187A. Color, lower surface: Close to 187B; proximally, close to 183B.

Inflorescence description:

*Appearance and flowering habit*.—Daisy-type inflorescences with ray and disc florets developing acropetally on a receptacle; inflorescences positioned above and beyond the foliar plane on strong peduncles; inflorescences face mostly upright; freely flowering habit with typically about 40 inflorescences developing per plant.

*Fragrance*.—None detected.

*Time to flower*.—Early flowering habit; plants begin flowering about 60 days after planting; flowering continuous during the summer and autumn in The Netherlands.

*Post-production longevity*.—Good postproduction longevity; inflorescences maintain good substance for about twelve days on the plant and for about five days as a cut flower; inflorescences persistent.

*Inflorescence buds*.—Height: About 1.6 cm. Diameter: About 1.9 cm. Shape: Oblate. Color: Close to 153A; towards the apex, close to 60A; towards the base, close to 146A.

*Inflorescence diameter*.—About 8.9 cm.

*Inflorescence depth* (*height*).—About 2.1 cm.

*Disc diameter*.—About 2 cm.

*Receptacle height*.—About 1 cm.

*Receptacle diameter*.—About 1.6 cm.

*Receptacle color*.—Close to 146A.

*Ray florets*.—Number of ray florets per inflorescence: About eight arranged in a single whorl. Length: About 3.9 cm. Width: About 2.6 cm. Shape: Broadly ovate. Apex: Mucronulate. Base: Attenuate. Margin: Entire. Aspect: Initially upright to roughly perpendicular to the peduncle. Texture, upper and lower surfaces: Smooth, glabrous; velvety. Color: When opening, upper surface: Close to 46A. When opening, lower surface: Close to 46A; towards the margins, close to 46B. Fully opened, upper and lower surfaces: Close to 46A; color does not fade with development.

*Disc florets*.—Number of disc florets per inflorescence: About 80. Length: About 1.7 cm. Diameter: About 2 mm. Shape: Tubular; apex dentate. Color, immature: Apex: Close to 183A. Mid-section: Close to 183B. Base: Close to 2C. Color, mature: Apex: Close to 21A. Mid-section: Close to 183B. Base: Close to 2D.

*Phyllaries*.—Quantity per inflorescence: About five arranged in a single whorl. Length: About 1.8 cm. Width: About 6 mm. Shape: Ovate. Apex: Obtuse. Base: Attenuate. Margin: Entire. Texture, upper and lower surfaces: Smooth, glabrous. Color, upper surface: Close to 200A. Color, lower surface: Close to 147A tinged with close to 200A.

*Peduncles*.—Length, terminal peduncle: About 25 cm. Length, fourth peduncle: About 14 cm. Length, seventh peduncle: About 6 cm. Diameter: About 1.1 cm. Strength: Strong. Aspect: Mostly erect. Texture: Smooth, glabrous. Color: Close to 187A.

*Reproductive organs*.—Androecium, present on disc florets only: Quantity per disc floret: Five. Filament length: About 4 mm. Filament color: Close to 2C. Anther shape: Lanceolate. Anther length: About 3 mm. Anther color: Close to 15A. Pollen amount: Abundant. Pollen color: Close to 21A. Gynoecium, present on ray and disc florets: Quantity per floret: One. Pistil length: About 6 mm. Stigma shape: Lanceolate. Stigma color: Close to 12B. Style length: About 5 mm. Style color: Close to 150C. Ovary color: Close to 150D. Fruits: Length: About 2.2 cm. Diameter: About 1.9 cm. Texture: Smooth, glabrous. Color: Close to 187B. Seeds: Length: About 7 mm. Diameter: About 1 mm. Color: Close to 187B.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'HDSC18' as illustrated and described.

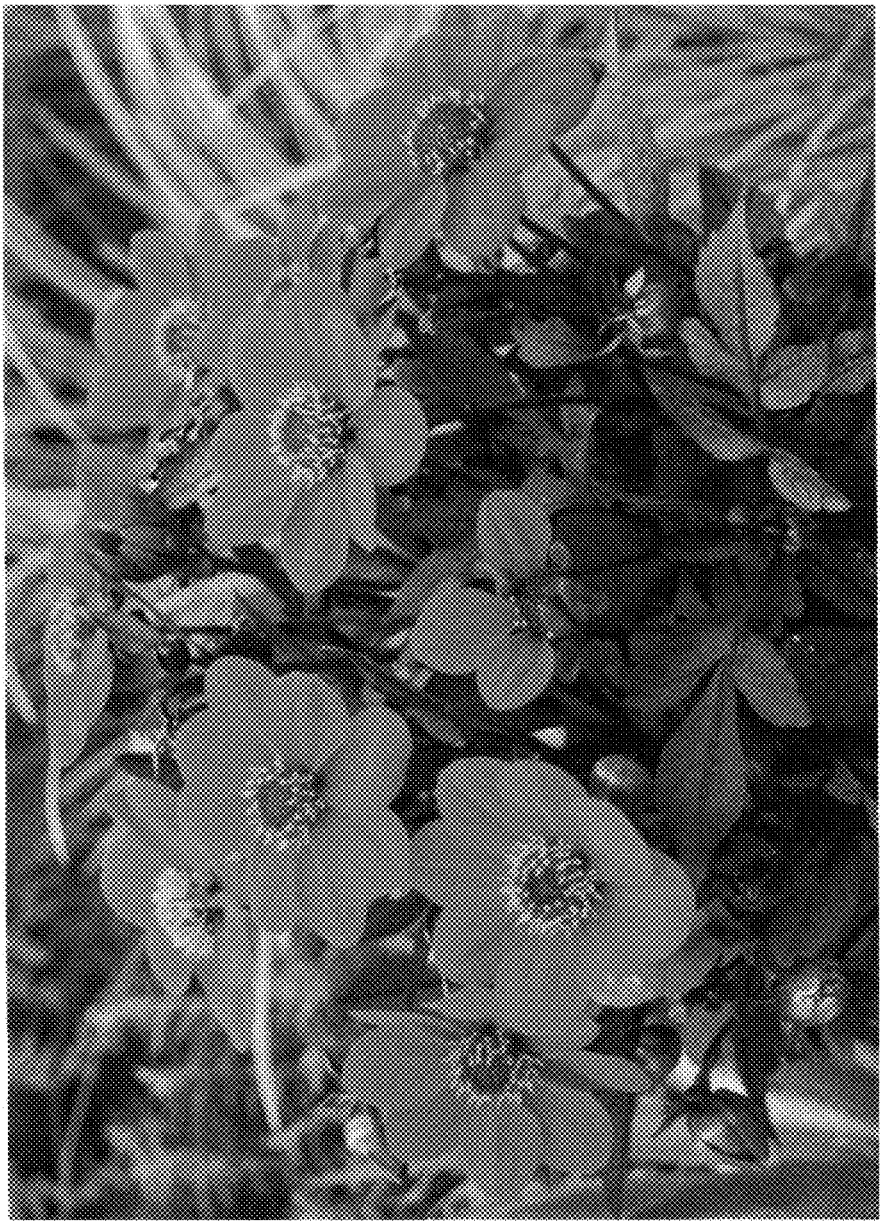

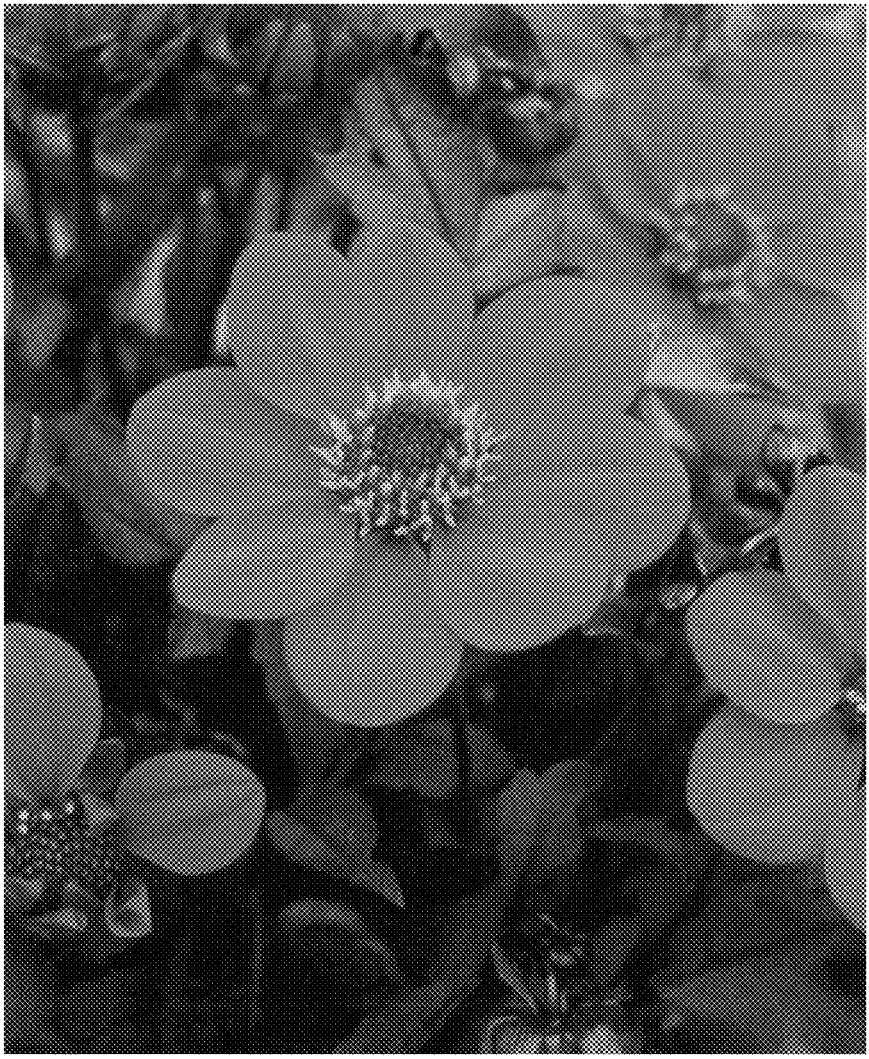

* * * * *